May 21, 1974
K. D. BUTTERS
Plant Pat. 3,553
CHRYSANTHEMUM PLANT
Filed April 3, 1972
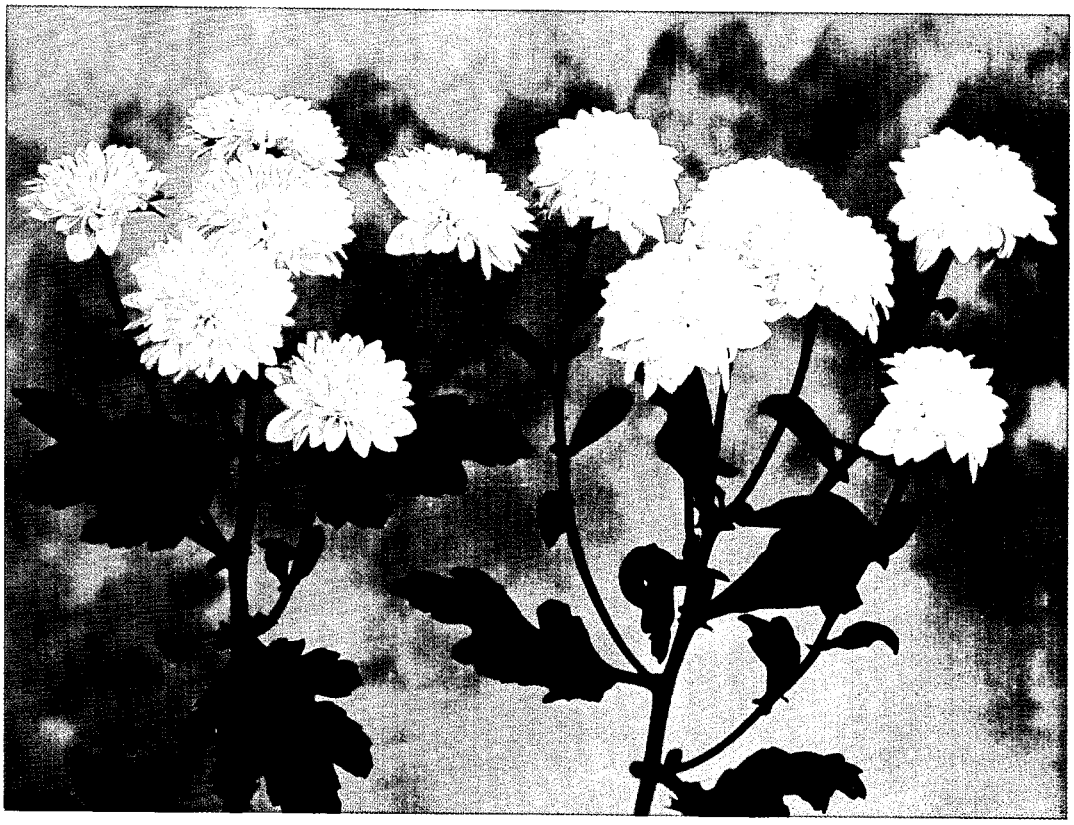

United States Patent Office

Plant Pat. 3,553

Patented May 21, 1974

3,553

CHRYSANTHEMUM PLANT

Keith D. Butters, Littlehampton, England, assignor to Yoder Brothers, Inc., Barberton, Ohio

Filed Apr. 3, 1972, Ser. No. 240,860

Int. Cl. A01h *5/00*

U.S. Cl. Plt.—78 1 Claim

The present invention comprises a new and distinct cultivar of chrysanthemum plant which is a sport of the well-known unpatented by commercial cultivar known in the United States as Hurricane.

The new cultivar is generally distinguished from the Hurricane family by its darker yellow color and superior color retention. In the Hurricane family, Improved Yellower Hurricane, also a commercial but unpatented cultivar, is the closest cultivar for comparison purposes, with the new cultivar being similar to Improved Yellow Hurricane in the following characteristics:

1. Flower size.
2. Foliage shape.
3. Foliage color.
4. Ability to initiate and develop flower buds at temperatures of 56° and less.

The new sport was discovered and asexually reproduced by cuttings at Sussex, England, and has been found to retain its distinctive characteristics through successive propagations.

The new cultivar when grown in the vicinity of Barberton, Ohio, has a response period of approximately 10 weeks. The response time, blooming period, color, and total vigor may vary significantly with varying environmental conditions such as temperature, day length, and light intensity. Suggested flowering in the northern and western United States is from June through mid-November; in California, May through November, and in the far south, December through mid-May.

The accompanying drawing shows the unique characteristics of the new cultivar, the color being as nearly true as possible with color illustrations of this type. Golden Hurricane appears on the left of the drawing and Improved Yellow Hurricane on the right.

The following data is based on observations in a greenhouse at Barberton, Ohio. Color references are to the Munsell Color Book, 1963 edition, and comparisions have been made with Improved Yellow Hurricane. Where only a single value or description has been listed for the new cultivar, the same value or description applies also to the comparison cultivar.

| | Golden Hurricane | Improved Yellow Hurricane |
|---|---|---|
| Bloom: | | |
| Size | 2½" | |
| Fully expanded | 3" | |
| Borne | Terminal clusters on elongated pedicels | |
| Stems | Very sturdy | |
| Form | Decorative | |
| Permanence | 7–19 days | |
| Color: | | |
| Center of flower | Golden yellow, 6.25Y8.5/12 | Yellow, 7.5Y8.5/10. |
| Base of petals | Dark yellow, 7.5Y8.5/10 | Yellow, 7.5Y8.5/10. |
| Inside of petals | do | Yellow, 7.5Y8.5/10 to light yellow, 7.5Y9/6. |
| Reverse of petals | Yellow, 7.5Y8.50/6 | Pale yellow, 7.5Y9/4. |
| Tonality from a distance | Dark yellow | Light yellow. |
| Discoloration | do | Pale yellow. |
| Petals: | | |
| Texture | Smooth | |
| Appearance and form | Open at base, broad at mid-point—tapering to a sharp point. | |
| Arrangement | Composite, whorled on a single receptacle | |
| Persistance | Resist shatter | |
| Fragrance | Typical chrysanthemum | |
| Reproductive organs: | | |
| Stamen, anthers | None | |
| Pollen | do | |
| Arrangement | do | |
| Styles | Present | |
| Length | Short | |
| Ovaries | At base of petal attached to receptacle | |
| Plant: | | |
| Form | Herbaceous | |
| Growth | Upright | |
| Height | Approximately 39"–44" when given 2–4 long day weeks, with a total crop time of 12–14 weeks as defined in the Yoder Brothers, Inc. timetables for the various seasons. | Approximately 36"–40" when given 2–4 long day weeks, with a total crop time of 2–14 weeks as defined in the Yoder Brothers, Inc. timetables for the various seasons. |
| Spread | None when grown single stem to slight when grown pinched. | |
| Foliage: | | |
| Top side | Dark green, 10GY3/4 | |
| Size | 7" long, 4¼" wide | |
| Quantity | Numerous | |
| Shape | Spatulate lobed | |
| Texture | Smooth | |
| Ribs and veins | Prominent | |
| Edge | Deeply indented | |
| Serration | Moderate | |
| Underside | Light green, 7.5GY5/4 | |
| Stipules | Prominent | |

The new cultivar is distinguished from Improved Yellow hurricane by the following characteristics:

1. Darker yellow flower color and superior color retention. Improved Yellow Hurricane oxidizes its color very rapidly as it opens.
2. 3"–4" more vigor.
3. 4–6 days later response.
4. Smoother flower form with less reflexing at maturity.

I claim:

1. A new and distinct variety of pompon chrysanthemum which is distinguished from the Hurricane family by its darker yellow color and its superior color retention, and is distinguished from the cultivar Improved Yellow Hurricane by its 3"–4" more vigor, 4–6 days later response, and a smoother flower form with less reflexing at maturity.

No references cited.

ROBERT E. BAGWILL, Primary Examiner

UNITED STATES PATENT OFFICE

CERTIFICATE OF CORRECTION

Patent No. PP-3553 Dated May 21, 1974

Inventor(s) KEITH D. BUTTERS

It is certified that error appears in the above-identified patent and that said Letters Patent are hereby corrected as shown below:

Column 1, line 12, "by" should be --but--.

In the tabulated description below Columns 1 and 2, below "Plant:", opposite "Height", under the cultivar "Improved Yellow Hurricane", "2-14 weeks" should be --12-14 weeks--.

Signed and sealed this 5th day of November 1974.

(SEAL)
Attest:

McCOY M. GIBSON JR.
Attesting Officer

C. MARSHALL DANN
Commissioner of Patents

USCOMM-DC 60376-P69
★ U.S. GOVERNMENT PRINTING OFFICE : 1969 O—366-114